United States Patent [19]

Youssefyeh et al.

[11] Patent Number: 4,959,485

[45] Date of Patent: Sep. 25, 1990

[54] HEXAHYDRODIBENZOFURAN CARBOXYLIC ACID DERIVATIVES

[75] Inventors: Raymond D. Youssefyeh, Princeton Junction, N.J.; Henry F. Campbell, North Wales; Donald E. Kuhla, Doylestown, both of Pa.

[73] Assignee: Rorer Pharmaceutical Corporation, Fort Washington, Pa.

[21] Appl. No.: 351,625

[22] Filed: May 15, 1989

Related U.S. Application Data

[62] Division of Ser. No. 186,824, Apr. 27, 1988, Pat. No. 4,863,921.

[51] Int. Cl.$^5$ .......................................... C07D 307/91
[52] U.S. Cl. .................................................. 549/461
[58] Field of Search ........................................ 549/461

[56] References Cited

PUBLICATIONS

Gilman et al., I, J. A. C. S., 57, pp. 2095–99 (1935).
Gilman et al., II, J. A. C. S., 61, pp. 951–954 (1939).
Keumi et al., Fukui Daigaku Kugakubu Seni Kugyo Kenkyu Shisetsu Hokoku, 14, pp. 71–77 (1976); Chem. Abstracts, 88, 152329u (1978).
Oita et al., J. Org. Chem. 20, pp. 657–667 (1955); Chem. Abstracts, 50, 7771a–7772a (1950).

Primary Examiner—John M. Ford
Assistant Examiner—Bernard I. Dentz
Attorney, Agent, or Firm—James A. Nicholson; Imre J. Balogh

[57] ABSTRACT

This invention is directed to certain dibenzofurancarboxamides and their use as 5HT$_3$ antagonists having unique CNS, anti-emetic and gastric prokinetic activity void of any significant D$_2$ receptor binding properties. This invention also describes novel processes necessary for their preparation.

11 Claims, No Drawings

HEXAHYDRODIBENZOFURAN CARBOXYLIC ACID DERIVATIVES

This application is a divisional of Ser. No. 186,824 filed Apr. 27, 1988, now U.S. Pat. No. 4,863,921.

FIELD OF THE INVENTION

This invention is directed to certain specific novel chemical compounds and their valuable use as pharmaceutical agents as 5HT$_3$ antagonists having unique CNS, anti-emetic and gastric prokinetic activity void of any significant D$_2$ receptor binding properties. This invention also describes novel processes necessary for their preparation.

SUMMARY OF THE INVENTION

This invention relates to the compounds described by general Formula I and to therapeutic compositions comprising as active ingredient a compound of Formula I:

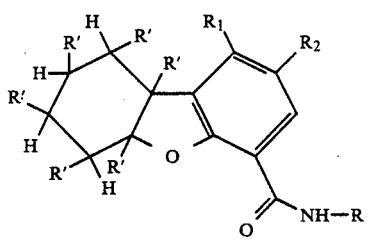

FORMULA I where
R$_1$ is hydrogen, amino or alkylamino, halo;
R$_2$ is hydrogen, halo, sulfamyl, alkylsulfamyl or alkylsulfonyl;
R' is hydrogen or alkyl or together with a vicinal R' group may form a double bond; and
R is

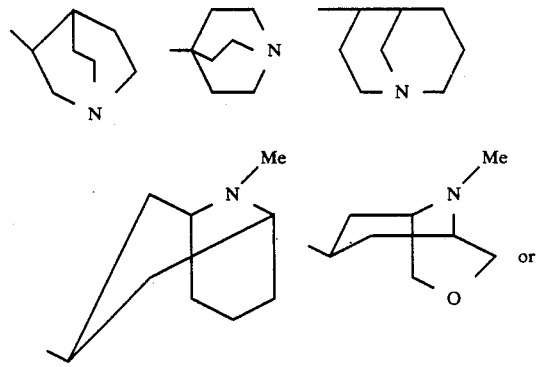

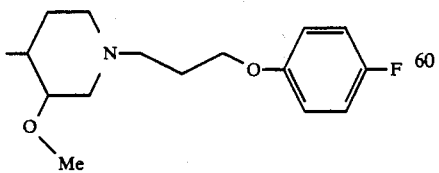

and pharmaceutically acceptable salts thereof.

The following nomenclature is used in the description of this invention.

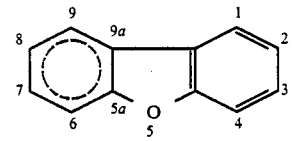

which refers to saturated, partially saturated and unsaturated compounds described herein. Preferred compounds of this invention include those compounds of Formulae II, III and IV.

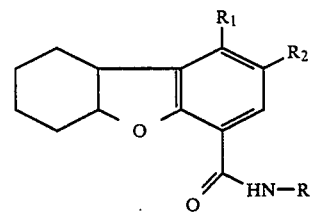

II

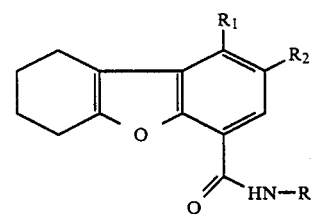

III

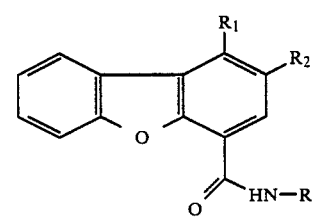

IV where R$_1$ and R$_2$ are as described above and R is

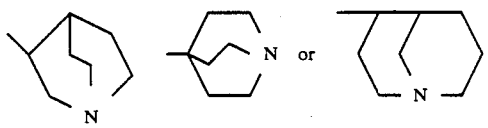

More preferred compounds include those of Formulae II, III and IV where
R$_1$ is amino, loweralkylamino or halo and R$_2$ is hydrogen;
R$_1$ is hydrogen and R$_2$ is halo, or
R$_1$ is amino and R$_2$ is halo.

The most preferred compounds include those of Formula II and especially where halo is chloro or bromo and loweralkyl is methyl.

The present compounds may be prepared by the following general procedure.

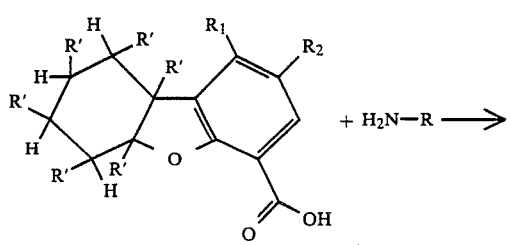

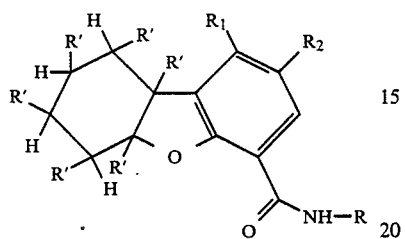

Condensation of a substituted dibenzofuran-4-carboxylic acid or a 6,7,8,9-tetrahydrodibenzofuran-4-carboxylic acid or a 5a,6,7,8,9,9a-hexahydrodibenzofuran-4-carboxylic acid or their acid halides or esters with an amine of the formula $H_2N$-R results in the corresponding carboxamide.

In general this reaction may be carried out at decreased temperatures, such as 0° C. by adding ethyl chloroformate to a reaction mixture of the acid in chloroform in the presence of triethylamine. This is then reacted with the amine of the formula $H_2N$-R to obtain the desired product. Condensation may also be carried out in the presence of a dehydrating catalyst such as a carbodiimide in a solvent at normal temperatures.

The starting materials, that is the substituted dibenzofuran-4-carboxylic acids, 6,7,8,9-tetrahydrobenzofuran-4-carboxylic acids and the 5a,6,7,8,9,9a-hexahydrodibenzofuran-4-carboxylic acids are also novel. They may be prepared by the following reaction schemes.

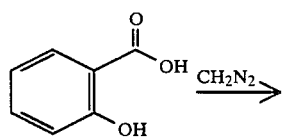

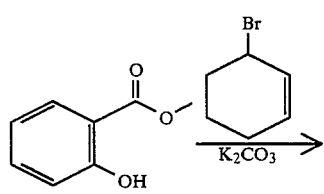

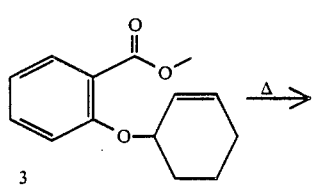

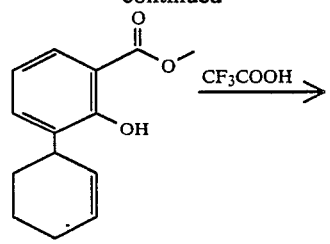

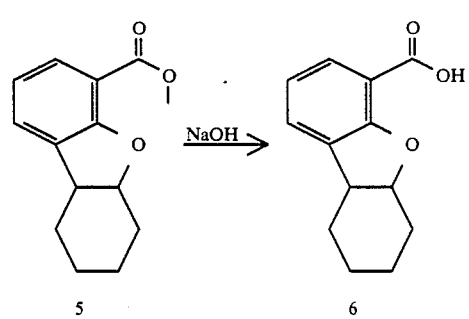

Salicylic acid is first esterified and then the phenol(2) is treated with 3-bromocyclohexene under basic conditions in a polar medium to obtain the phenyl cyclohexenyl ether(3), Claisen rearrangement at high temperature results in the methyl 3-(3'-cyclohexene)-salicylate(4). Ring closure using trifluoroacetic acid results in the formation of the 5a,6,7,8,9,9a-hexahydrodibenzofuran ring(5). This may then be hydrolyzed to the acid (6) with aqueous base.

When the 5a,6,7,8,9,9a-hexahydrodibenzofuran-4-carboxylate(5) is oxidized with DDQ, dichlorodicyanoquinone, the resultant double bond of the furan ring is formed to obtain 6,7,8,9-tetrahydrodibenzofuran-4-carboxylate(7). Excess DDQ can result in the unsaturated dibenzofuran-4-carboxylate product(8).

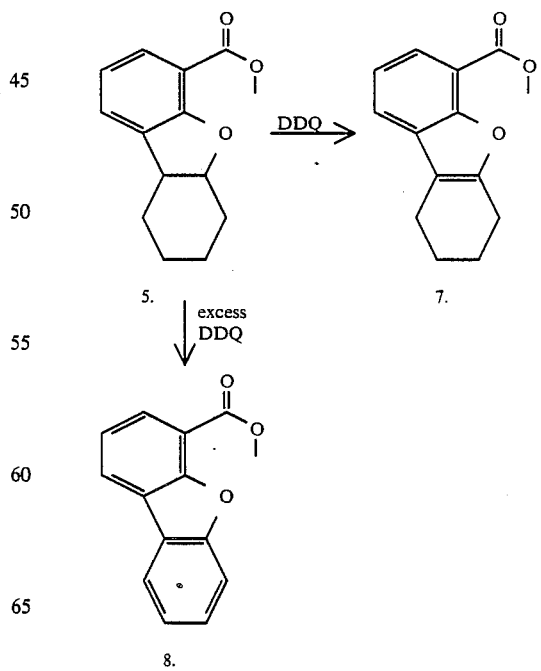

Dehydrogeneration of 6,7,8,9-tetrahydrodibenzofuran-4-carboxylate(7) with palladium on carbon catalyst at raised temperatures (230°–240° C.) results in the dibenzofuran-4-carboxylate(8).

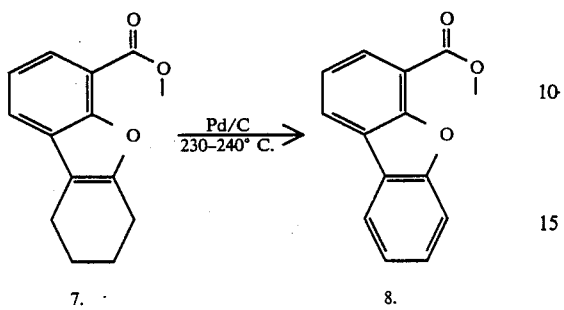

Deesterification of the esters 7 and 8 may be carried out with aqueous base, as above.

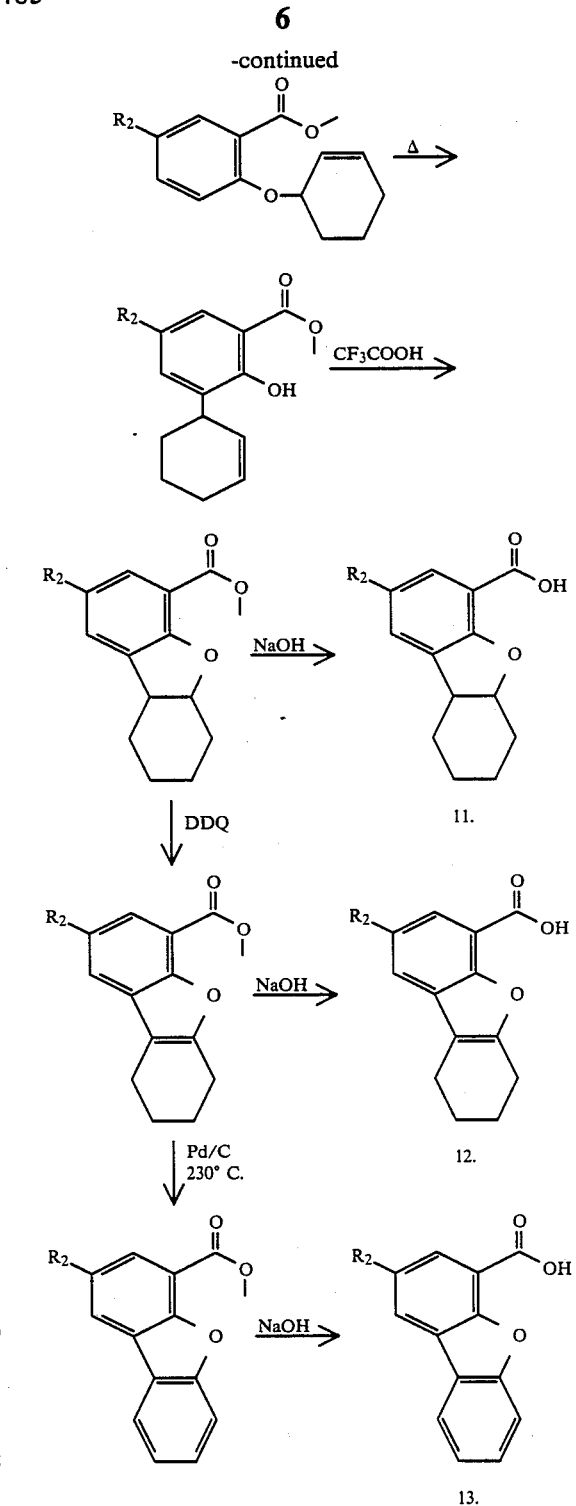

When $R_2$ substituted is desired the above reactions may be carried out starting with the proper 5-substituted salicyclic acid. Thus the following reaction sequences may take place as above.

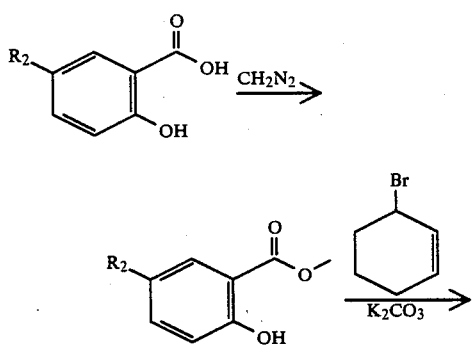

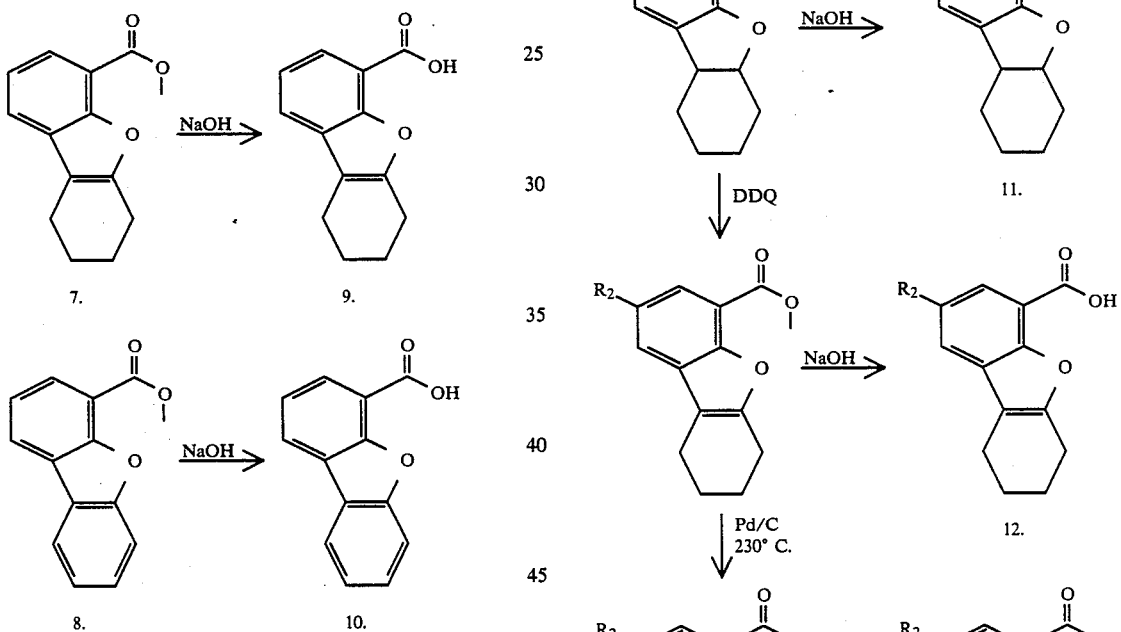

When $R_1$ substitution is halo the above reaction sequence may be carried out starting with 4-halo salicyclic acid.

In the case where $R_2$ is sulfamyl it is best that this group be protected initially with an acetyl group or the like and then deacetylated.

When $R_1$ is an amine function this also should be protected with an acetyl group or the like and then deacetylated after the dibenzofuran ring system has been formed.

Treatment of a 4-amino or 4-alkylamino salicylic acid with MeOH/HCl followed by acetylation with acetyl chloride in pyridine in the usual manner results in the 4-acetylamino or 4-acetylalkylaminosalicylates(14). Demethylation of the alcohol and ester is then carried out using boron tribromide in a non polar solvent to obtain the 4-acetylamino or 4-acetylalkylaminosalicylic acids(15). Esterification is accomplished with diazomethene as before and the resultant ester is used in a similar manner as above to obtain the desired 1-amino or alkylamino dibenzofuran-4-carboxylic acid compounds(18, 21, and 24).

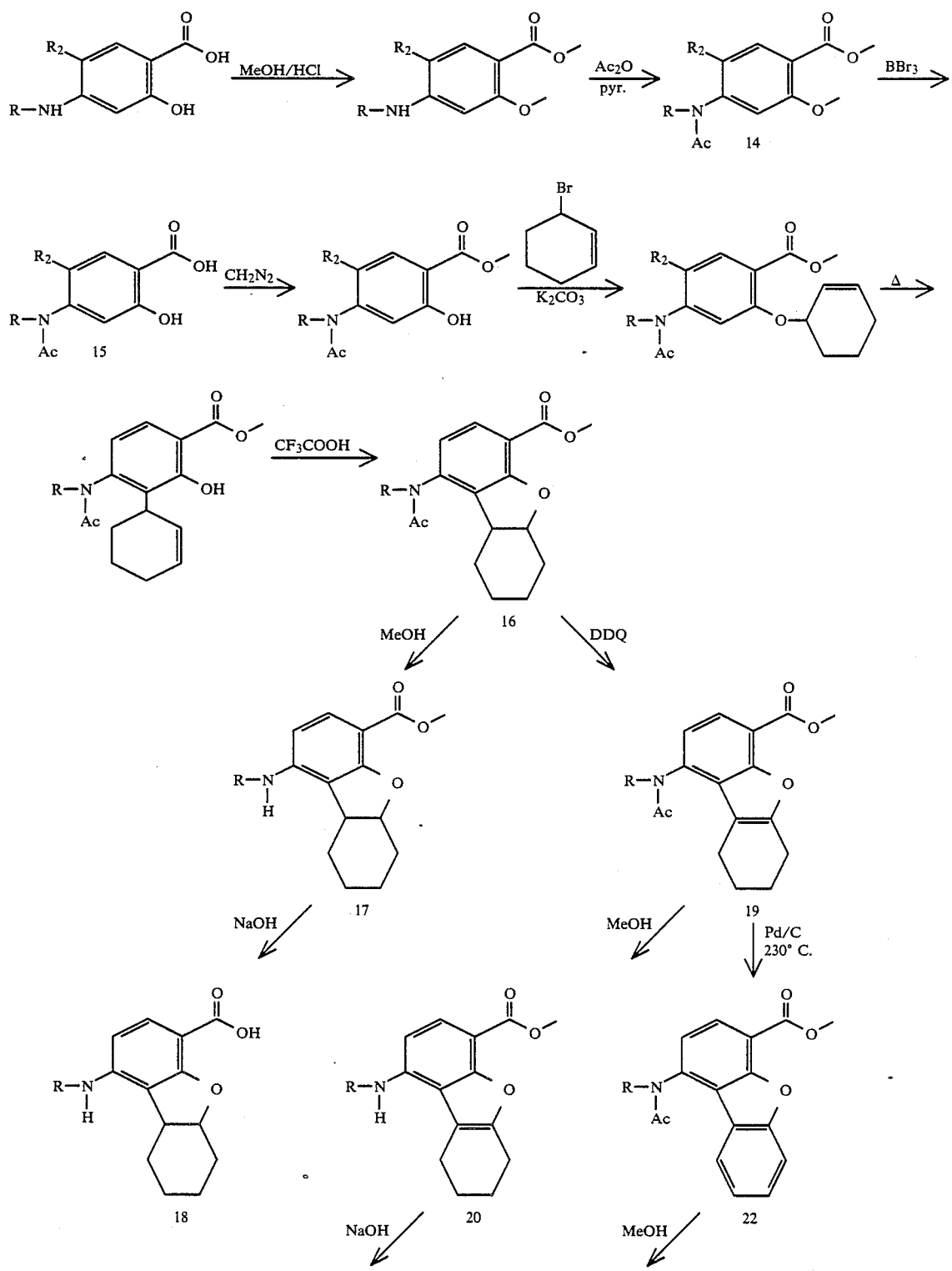

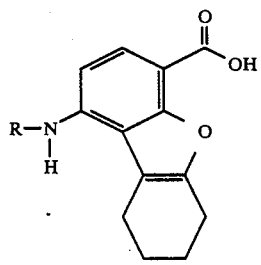
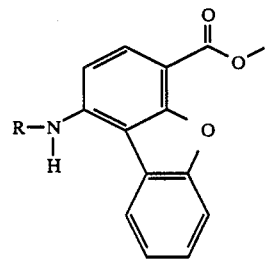
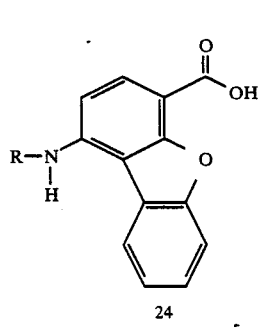
where R is H or alkyl.
In a similar manner, when $R_1$ and $R_2$ are both substituted with groups other than hydrogen the following reaction sequences are possible to obtain compounds 27, 30 and 33.
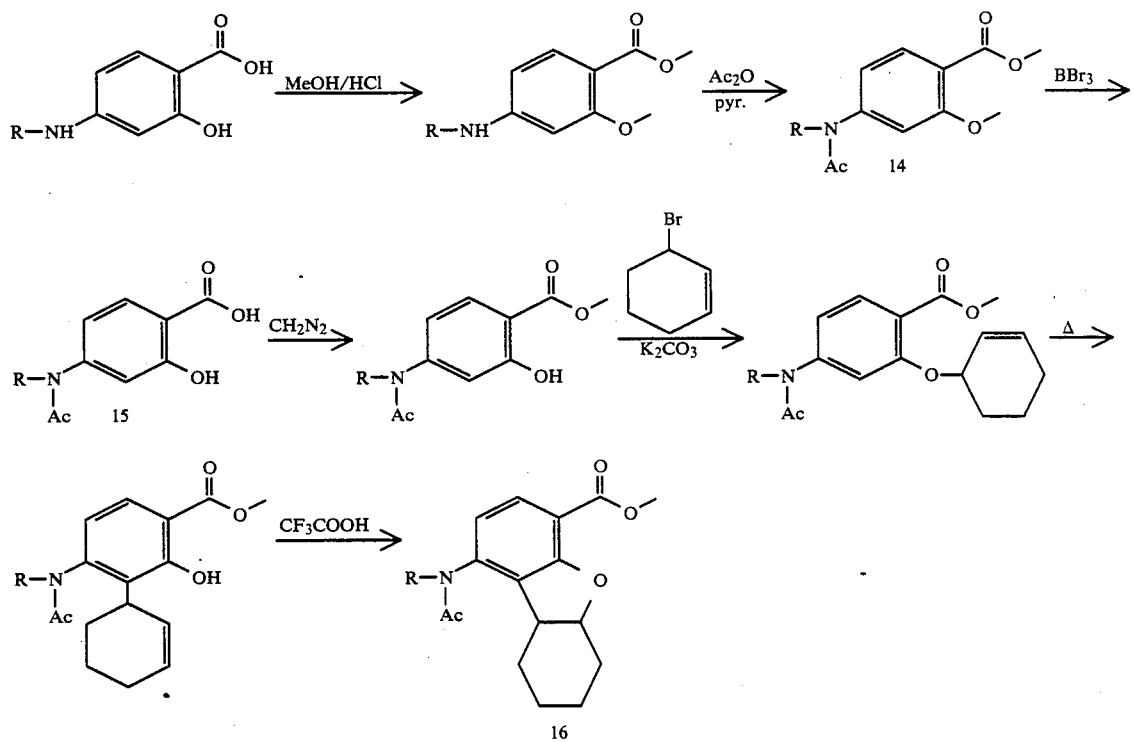

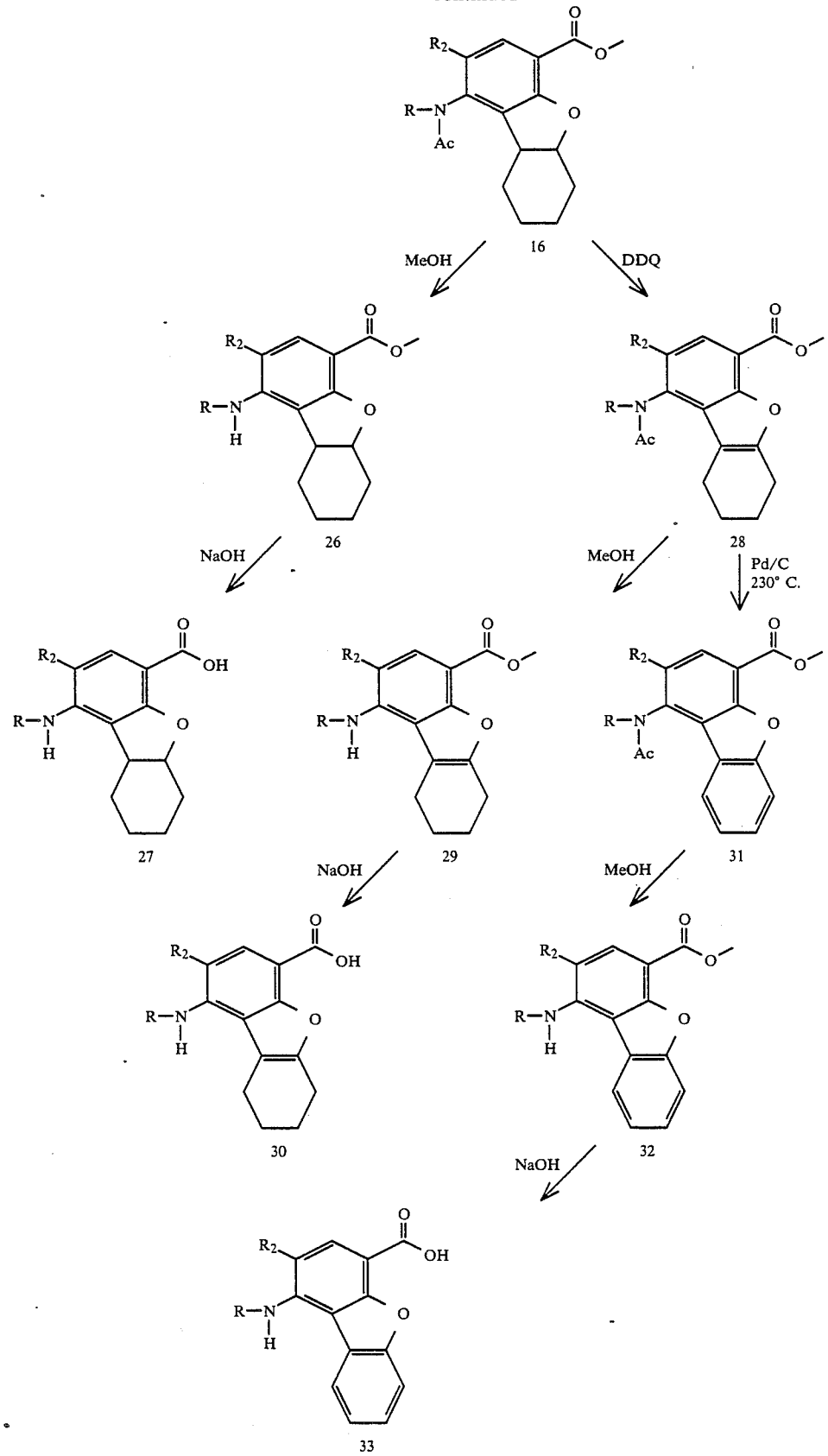
-continued
When it is desired to have R' substitution of lower alkyl then a suitable starting material should be used. Thus for example if the final product desired is 1-amino- 2-chloro-8-methyl-5a,6,7,8,9,9a-hexahydrodibenzofuran-4-carboxylic acid(34) then 3-bromo-5-methylcyclohexene should be used as reagent in place of 3-bromocyclohexene.

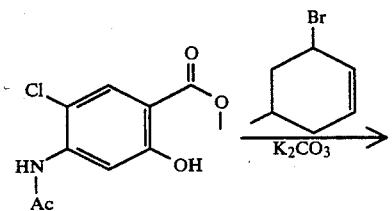

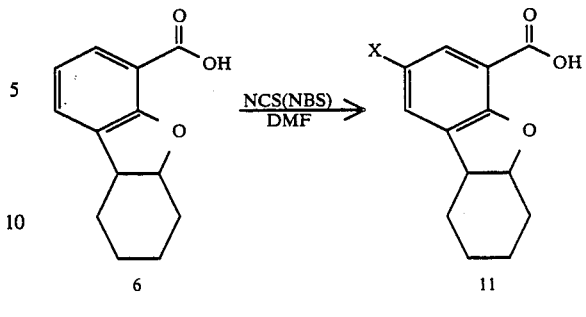

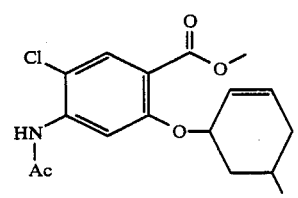

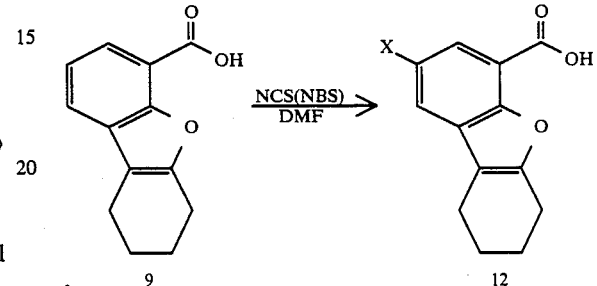

Following the above sequence of steps of the final product would be

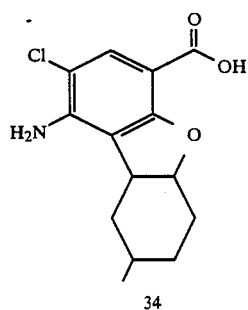

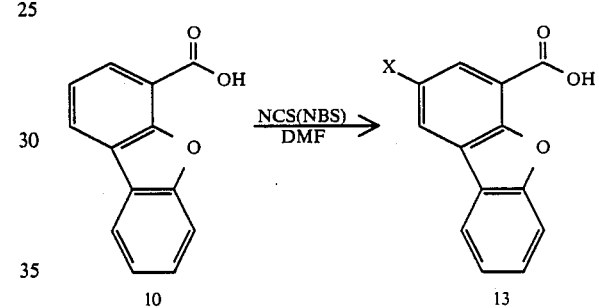

where X is cloro or bromo.

In a similar manner other compounds having R' substitution may be prepared.

When the 4-carboxylic acids 6, 9 and 10 are treated with N-chlorosuccinic or N-bromosuccinimide in a polar medium (DMF) at room temperature, the resulting halogenated products 11, 12 and 13 are formed.

Halogenation may also be carried out on the 1-acetylamino compounds of the esters 16, 19 and 22. Halogenation occurs in the 2-position. When these halogenated products are treated with base as above, hydrolysis gives the desired 1-amino-2-halo-4-carboxylic acids 27, 30 and 33 of this invention.

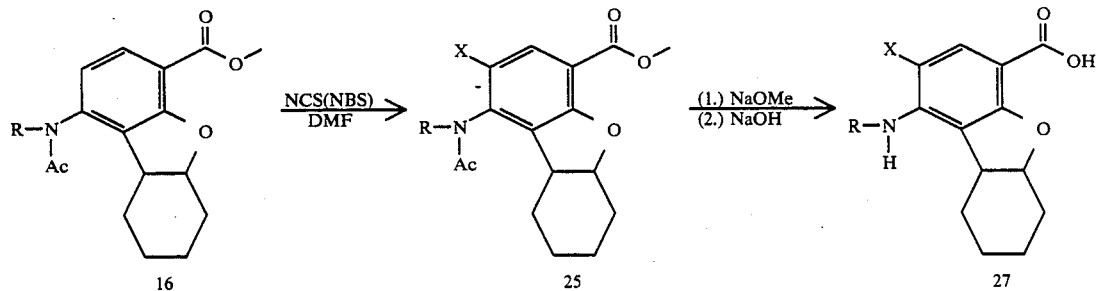

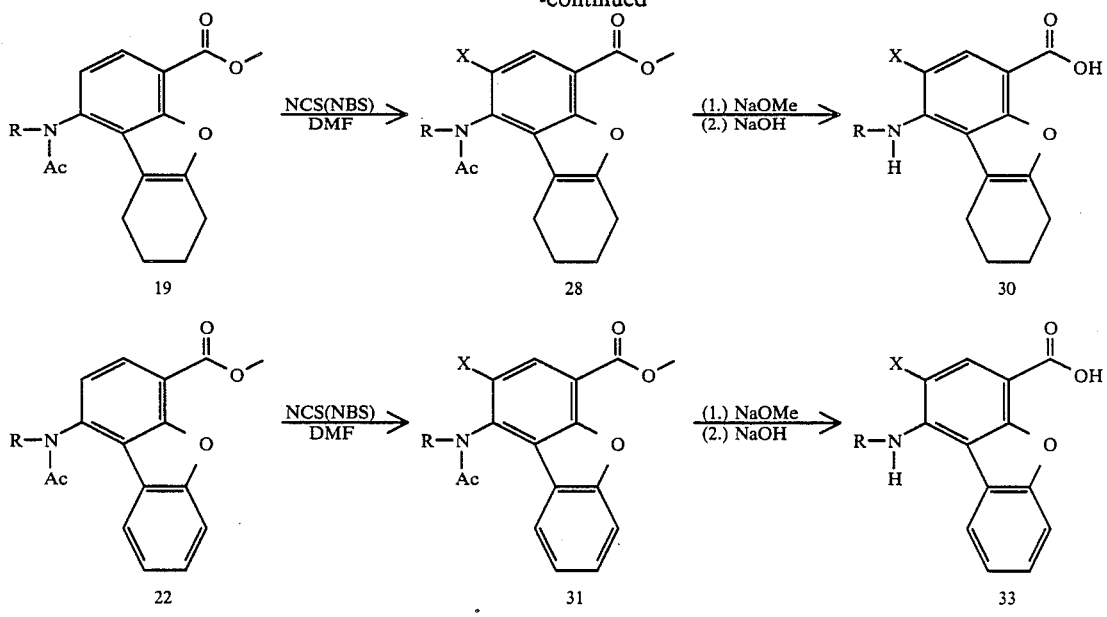

Certain compounds of this invention have at least one asymmetric carbon atom, such as the 5a,6,7,8,9,9a-hexahydrodibenzofuran compounds or those compounds wherein at least one R' is other than hydrogen or still those compounds were the R group contains an asymmetric carbon atom. As a result, those compounds of Formula I may be obtained either as racemic mixtures or as individual enantiomers. When two asymmetric centers are present the product may exist as a mixture of two diasteromers. The product may be synthesized as a mixture of the isomers and then the desired isomer separated by conventional techniques such as chromatography or fractional crystallization from which each diasteriomer may be resolved. On the other hand, synthesis may be carried out by known sterospecific processes using the desired form of the intermediate which would result in obtaining the desired specificity.

In the case where R contains an asymmetric carbon atom it is convenient to carry out condensation of 5a,6,7,8,9,9a-hexahydrodibenzofuran-4-carboxylic acid with 3-amino-1-azabicyclo-[2.2.2.]-octane or the like using the sterospecific materials. Thus, the hexahydrodibenzofuran-4-carboxylic acid is resolved prior to condensation with resolved 3-aminoquinuclidine.

Further, certain compounds of this invention may exist in their cis or trans configuration with respect to the furan ring.

The compounds of this invention may be readily converted to their non-toxic acid addition salts by customary methods in the art. The non-toxic salts of this invention are those salts the acid component of which is pharmacologically acceptable in the intended dosages, including those prepared from inorganic acids such as hydrochloric acid, hydrobromic acid, sulfuric acid, nitric acid and phosphoric acid, and from organic acids such as methane sulfonic acid, benzenesulfonic acid, acetic acid, propionic acid, maleic acid, oxalic acid, succinic acid, glycolic acid, lactic acid, salicylic acid, benzoic acid, nicotinic acid, phthalic acid, stearic acid, oleic acid, abietic acid, etc.

We have found that the compounds of this invention have gastric prokinetic and anti-emetic properties and lack $D_2$-receptor binding activity. As such they possess therapeutic value in the treatment of upper bowel motility and gastroesophageal reflux disorders. Further, the compounds of this invention may be useful in the treatment of disorders related to impaired gastrointestinal motility such as retarted gastric emptying, dyspepsia, flatulence, esophageal reflux, peptic ulcer and emesis. The compounds of this invention exhibit 5-$HT_3$ antagonism and are considered to be useful in the treatment of psychotic disorders such as schizophrenia and anxiety and in the prophylaxis treatment of migraine and cluster headaches. We have further found that these compounds are selective in that they have little or no dopaminergic antagonist activity.

Various tests in animals can be carried out to show the ability of the compounds of this invention to exhibit pharmacological responses that can be correlated with activity in humans. These tests involve such factors as the effect of the compounds of Formula I on gastric motility, emesis, selective antagonism of 5-$HT_3$ receptors and their $D_2$ dopamine receptor binding properties.

It has been found that the compounds of this invention when tested in the above variety of situations show a marked activity.

One such test is the "Rat Gastric Emptying: Amberlite Bead Method". This test is carried out as follows:

The study is designed to assess the effects of a test agent on gastric emptying of a solid meal in the rat. The procedure is a modification of those used in L. E. Borella and W. Lippmann (1980) *Digestion* 20: 26–49.

Procedure

Amberlite ® beads are placed in a phenol red solution and allowed to soak for several hours. Phenol red serves as an indicator, changing the beads from yellow to purple as their environment becomes more basic. After soaking, the beads are rinsed with 0.1 NaOH to make them purple and then washed with deionized water to wash away the NaOH.

The beads are filtered several times through 1.18 and 1.4 mm sieves to obtain beads with diameters in between these sizes. This is done using large quantities of deionized water. The beads are stored in saline until ready to use.

Male Sprague-Dawley rats are fasted 24 hours prior to the study with water ad libitum. Rats are randomly divided in treatment groups with an N of 6 or 7.

Test agents are prepared in 0.5% methylcellulose and administered to the rats orally in a 10 ml/kg dose volume. Control rats receive 0.5% methylcellulose, 10 ml/kg p.o. One hour after dosing, rats are given 60 Amberlite ® beads intragastrically. The beads are delivered via a 3 inch piece of PE 205 tubing attached to a 16 gauge tubing adapter and syringe. A small piece of PE 50 tubing is placed inside the tubing adapter to prevent the beads from being pulled back into the syringe. The beads are flushed into each rat's stomach with 1 ml saline.

Rats are sacrificed 30 minutes after receiving the beads and their stomachs are removed. The number of beads remaining in each stomach is counted after rinsing the beads with NaOH.

The number of beads remaining in each stomach is subtracted from 60 to obtain the number of beads emptied. The mean number of beads ±S.E.M. is determined for each treatment group. The percent change from control is calculated as follows:

$$\frac{\text{Mean Control Group} - \text{Mean Test Agent Group}}{\text{Mean Control Group}} \times 100$$

Statistical significance may be determined using a t-test for independent samples with a probability of 0.05 or less considered to be significant.

In order to demonstrate the ability of the compounds of this invention as anti-emetic agents the following test for "Cisplatin-Induced Emesis in the Ferret" may be used. This test is a modified version of a paper reported by A. P. Florezyk, J. E. Schurig and W. T. Brodner in *Cancer Treatment Reports*: Vol. 66, No. 1. January 1982.

Cisplatin had been shown to cause emesis in the dog and cat. Florczyk, et al. have used the ferret to demonstrate the same effects.

Procedure

Male castrated, Fitch ferrets, weighing between 1.0 and 1.5 kg have an in Indwelling catheter placed in the jagular vein. After a 2-3 day recovery period, the experimental procedure is begun.

30 minutes prior to administration of cisplatin, ferrets are dosed with the compound in 0.9% saline (i.v.) at a dose volume of 2.0 ml/kg.

45 minutes after administration of cisplatin, ferrets are again dosed with the 0.9% saline (i.v.) mixture at a dose volume of 2.0 ml/kg.

Cisplatin is administered (i.v.) 30 minutes after the first dosing with the 0.9% saline. Cisplatin, 10 mg/kg is administered in a dose volume of 2.0 ml/kg.

The time of cisplatin administration is taken as time zero. Ferrets are observed for the duration of the experiment (4 hours). The elapsed time to the first emetic episode is noted and recorded, as are the total number of periods of emesis.

An emetic (vomiting) episode is characterized by agitated behavior, such as pacing around the cage and rapid to and fro movements. Concurrent with this behavior are several retching movements in a row, followed by a single, large, retch which may or may not expulse gastric contents. Immediately following the single large retch, the ferret relaxes. Single coughs or retches are not counted as vomiting episodes.

D-2 Dopamine Receptor Binding Assay

The D-2 dopamine receptor binding assay has been developed with slight modifications using the method of Ian Cresse, Robert Schneider and Solomon H. Snyder, *Europ. J. Pharmacol.* 46: 377–381(1977). Spiroperidol is a butyrophenone neuroleptic whose affinity for dopamine receptors in brain tissue is greater than that of any other known drug. It is a highly specific D-1 dopamine (non-cyclase linked) receptor agent with $K_1$ values of 0.1–0.5 for D-2 inhibition and 300 nM for D-1 inhibition.

Sodium ions are important regulators of dopamine receptors. The affinity of the D-2 receptor is markedly enhanced by the presence of millimolar concentrations of sodium chloride. The Kd in the absence and presence of 120 mM sodium chloride is 1.2 and 0.086 nM respectively. Sodium chloride (120 mM) is included in all assays as a standard condition.

The caudate nucleus (corpus striatum) is used as the receptor source because it contains the highest density of dopamine receptors in the brain and periphery.

Procedure

Male Charles-River rates weighing 250–300 g are decapitated and their brains removed, cooled on ice, and caudate dissected immediately and frozen on dry ice. Tissue can be stored indefinitely at −70° C. For assay caudate is homogenized in 30 ml of tris buffer (pH 7.7 at 25° C.) using the polytron homogenizer. The homogenate is centrifuged at 40,000 g (18,000–19,000 RPM in SS-34 rotor) for 15 minutes. Pellet is resuspended in fresh buffer and centrifuged again. The final pellet is resuspended in 150 volumes of assay buffer.

Specific $^3$H-spiroperidol binding is assayed in a total 2 ml reaction volume consisting of 500 $\mu$l of caudate homogenate, 50 mM tris buffer (pH 7.4 at 35° C.), 5 mM $MgSO_4$, 2 mM EDTA.2NA, 120 mM NaCl, 0.1% ascorbic acid, 0.4 nM $^3$H-spiroperidol and test compound or assay buffer. When catecholamines are included in the assay, 10 $\mu$M pargyline should be included in the reaction mixture to inhibit monoamine oxidase. Samples are incubated at 37° C. for 30 minutes followed by addition of 5 ml ice cold 50 mM TRIS (pH 7.7 at 25° C.) and filtration through GF/B glass fiber filters on a Brandel Receptor Binding Filtration apparatus. Filters are washed twice with an additional 5 ml of tris buffer each. Assay groups are performed in triplicate and 1 $\mu$M d(+) butaclamol is used to determine nonspecific binding. Filters are placed in vials containing 10 ml of Ecoscint phosphor, shaken for 30 minutes and dpm determined by liquid scintillation spectrophotometry using a quench curve. Proteins are determined by the method of Bradford, M. Anal. Biochem 72, 248(1976) using Bio-Rad's coomassie blue G-250 dye reagent. Bovine gamma globulin supplied by BIO-RAD is used as the protein standard.

Bezold-Jarisch effect in anaesthetized rats

Male rats 260–290 g are anaesthetized with urethane 1.25 g/kg$^{-1}$ i.p., and the trachea cannulated. The jugular vein is cannulated for intravenous (i.v.) injection of drugs. Blood pressure is recorded from a cannula in the left carotid artery and connected to a haparin/saline-filled pressure transducer. Continuous heart rate measurements are taken from the blood pressure recordings.

The Bezold-Jarisch effect is evoked by rapid, bolus i.v. injections of 5-HT and measurements are made of the fall in heart rate. In each rate, consistent responses are first established with the minimum dose of 5-HT that evokes a clear fall in heart rate. Injections of 5-HT are given every 12 minutes and a dose-response curve for the test compound is established by injecting increasing doses of compound 5 minutes before each injection of 5-HT. The effect of the compound on the 5-HT-evoked bradycardia is calculated as a percent of the bradycardia evoked by 5-HT before injection of compound.

In separate experiments to measure the duration of 5-HT antagonism caused by the compounds of this invention, a single dose of compound is injected 5 minutes before 5-HT, and the effects of 7 repeated challenges with 5-HT are then monitored. The effects of the compound on the efferent vagal limb of the Bezold-Jarisch reflex are checked by electrically stimulating the peripheral end of a cut vagus nerve. Unipolar electrical stimulation is applied every 5 minutes via a pair of silver electrodes, using 1 ms rectangular pulses in 5 s trains with a maximally-effective voltage (20 V at 10 Hz). Pulse frequency may vary from 5–30 Hz and frequency-response curves are constructed before and 10 minutes after i.v. injection of a single dose of compound.

The results of these above tests indicate that the compounds for this invention exhibit a valuable balance between the peripheral and central action of the nervous system and may be useful in the treatment of disorders related to impaired gastro-intestinal motility such as gastric emptying, dyspepsia, flatulence, esophogeal reflux and peptic ulcer and in the treatment of disorders of the central nervous system such as psychosis.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepthelially including transdermal, opthalmic, sublingual and buccal; topically including opthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestibe tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelating; excipients such as dicalcium phosphate; a disintegrating agent such as corn starch, patato starch, lginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimersal, and the like. In many cases, it will be preferable to include isotonic agents, for example, sugars or sodium chloride. Prolonged absorption of the injectable compositions of agent delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vaccum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 20 mg or from about 0.01 mg to about 50 mg/kg of body weight per day and higher although it may be administered in several different dosage units from once to several times a day. Higher dosages are required for oral administration.

The compounds of this invention may be prepared by the following representative examples.

The compounds of the present invention may be prepared by the following representative examples.

EXAMPLE 1

Methyl 5-chlorosalicylate

To a cold solution of 100 ml methanol is slowly added 100 ml thionyl chloride followed by 30 g of 5-chlorosalicylic acid. This is then refluxed overnight, the solvent removed and the residue dissolved in ether. The ether is washed with a sodium bicarbonate solution, water, dried over magnesium sulfate and evaporated to dryness to obtain methyl 5-chlorosalicylate which is used directly in the next step.

EXAMPLE 2

Methyl 2-(cyclohexen-3-yloxy)-5-chlorobenzoate

A mixture of 18.6 g of methyl 5-chlorosalicylate, 28 g of $K_2CO_3$ and 20 g of 3-bromocyclohexene in 200 ml of DMF is stirred at 90° C. overnight. The mixture is then poured onto water, extracted with ethylacetate, washed with water, dried over magnesium sulfate and evaporated to dryness to obtain crude product. This is purified by flash chromatography using hexane as the eluent to give pure methyl 2-(cyclohexen-3-yloxy)-5-chlorobenzoate as the first fraction which is used directly in the next step.

EXAMPLE 3

Methyl 3-(3-hexenyl)-5-chlorosalicylate

Methyl 2-(cyclohexen-3-yloxy)-5-chlorobenzonate (4.5 g) is heated to 210° C. for 3 hours. The residue is dissolved in hexane and purified by flash chromatography using first hexanes as eluent and then 5% ethylacetate/hexane to give pure methyl 3-(3-hexenyl)-5-chlorosalicylate. This is used directly in the next step.

EXAMPLE 4

Methyl 2-chloro-5a,6,7,8,9,9a-hexahydrodibenzofuran-4-carboxylate

A mixture of 2.2 g of methyl 3-(3-hexenyl)-5-chlorosalicylate and 5 ml of trifluoroacetic acid are stirred at room temperature overnight. The acid is removed under vacuo and the residue diluted with ether, washed with sodium bicarbonate solution, then water and dried over magnesium sulfate and evaporated to dryness to give an oily product. Purification by flash chromatography using hexane as eluent gives first unreacted starting material and then methyl 2-chloro-5a,6,7,8,9,9a-hexahydrodibenzofuran-4-carboxylate. This is used directly in the next step without further purification.

EXAMPLE 5

2-Chloro-5a,6,7,8,9,9a-hexahydrodibenzofuran-4-carboxylic acid

A mixture of 1.6 g of methyl 2-chloro-5a,6,7,8,9,9a-hexahydrodibenzofuran-4-carboxylate in 10 ml of methanol and 20 ml of 1N sodium hydroxide is stirred at 50° C. for 6 hours. This is cooled, the methanol is removed under vacuo, diluted with 30 ml water and filtered. The aqueous solution is acidified with acetic acid, extracted with ethyl acetate, washed with water, dried over magnesium sulfate and evaporated to dryness to give crystalline product which is used directly in the next step.

EXAMPLE 6

2-Chloro-5a,6,7,8,9,9a-hexahydrodibenzofuran-4-(N-1-azabicyclo[2.2.2.]oct-3-yl)carboxamide To a cold solution of 1.3 g of 2-chloro-5a,6,7,8,9,9a-hexahydrodibenzofuran-4-carboxylic acid in 40 ml of chloroform is added 0.8 g of triethylamine at room temperature. To this is added 0.7 g of ethylchloroformate in 10 ml of chloroform and stirring continued for 1½ hours. This is added in one portion to a mixture of 15 g $K_2CO_3$ in 25 ml water containing 5 g of 3-aminoquinuclidine dihydrochloride. Stirring is continued overnight. The reaction mixture is diluted with 100 ml chloroform and the organic layer separated, washed twice with water, dried over magnesium sulfate and evaporated to dryness to give 1.2 g of oily product. The latter is purified by flash chromatography using 10% methanol/chloroform which results in pure 2-chloro-5a,6,7,8,9,9a-hexahydrodibenzofuran-4-(N-1-azabicylo-[2.2.2.]oct-3-yl)carboxylate.

Calculated: C 64.95; H 7.08; N 7.57; Found: C 64.24; H 6.72; N 7.02.

EXAMPLE 7

When 5-chlorosalicylic acid is replaced in Example 1 with salicylic acid, 5-bromosalicylic acid or 5-methylsulfonylsalicylic acid then the products prepared following the procedures of Examples 1–6 are 5a,6,7,8,9,9a-hexahydrodibenzofuran-4-(N-1-azabicylo[2.2.2-.]oct-3-yl)carboxamide; 2-bromo-5a,6,7,8,9,9a-hexahydrodibenzofuran-4-(N-1-azabicyclo[2.2.2.]oct-3-yl)carboxamide; and 2-methylsulfonyl-5a,6,7,8,9,9a-hexahydrodibenzofuran-4-(N-1-azabicyclo[2.2.2.]oct-3-yl)carboxamide.

EXAMPLE 8

Methyl 2-methoxy-4-amino-5-chlorobenzoate

To a solution of 50 g of 2-methoxy-4-amino-5-chlorobenzoic acid in 500 ml of methanol is added HCl gas until all the material dissolves. Stirring is continued overnight, the solvent removed, ether added, filtered, dried over magnesium sulfate and evaporated to dryness to obtain methyl 2-methoxy-4-amino-5-chlorobenzoate which is used directly in the next step.

EXAMPLE 9

Methyl 2-methoxy-4-acetylamino-5-chlorobenzoate

A mixture of 21 g of methyl 2-methoxy-4-amino-5-chlorobenzoate is stirred in 12 ml acetic anhydride and 100 ml acetic acid at 100° C. for 24 hours. The reaction mixture is filtered, diluted with water, filtered and evaporated to dryness to obtain methyl 2-methoxy-4-acetylamino-5-chlorobenzoate which is used directly in the next step.

EXAMPLE 10

4-Acetylamino-5-chlorosalicylic acid

To a mixture of 16 g of methyl 2-methoxy-4-acetylamino-5-chlorobenzoate in 130 ml of methylene chloride is slowly added 100 ml of a methylene chloride solution of borontribromide (250 g $BBr_3$ per liter) and stirring continued for 24 hours. 1N sodium hydroxide solution is then added until all material is dissolved. The two layers are separated and the aqueous layer is acidified with 1N hydrochloric acid, filtered, washed with water and evaporated to dryness to give 4-acetylamino-5-chlorosalicylic acid which is used directly in the next step.

EXAMPLE 11

Methyl 4-acetylamino-5-chlorosalicylate

To a mixture of 5 g of potassium hydroxide, 8 ml water and 25 ml ethanol at 0° C. (with no stirring) is slowly added a solution of 22 g Diazald in 200 ml ether. The combination of diazomethane in ether which is distilled over is cooled in an ice cold flask until the distillation is complete. To this solution is added 13 g of 4-acetylamino-5-chlorosalicylic acid in 150 ml THF. After ½ hour the excess diazomethane is decomposed by acetic acid and the mixture filtered to obtain crude methyl 4-acetylamino-5-chlorosalicylate. The filtrate is concentrated to obtain further product which is combined and used directly in the next step.

EXAMPLE 12

Methyl 2-(cyclohexen-3-yloxy)-4-acetylamino-5-chlorobenzoate

A mixture of 2.5 g methyl 4-acetylamino-5-chlorosalicylate, 2 g of 3-bromocyclohexene, 2 g $K_2CO_3$ and 30 ml DMF are combined and heated at 110° C. overnight. The reaction mixture is then poured into water, filtered, dried and then extracted into ether. The ether solution is treated with charcoal, filtered and evaporated to dryness to obtain methyl 2-(cyclohexen-3-yloxy)-4-acetylamino-5-chlorobenzoate. This is then purified by recrystallization from ether/hexane. (M.P. 100°–102° C.)

EXAMPLE 13

Methyl 3-(3-hexenyl)-4-acetylamino-5-chlorosalicylate

A mixture of 0.6 g of methyl 2-(cyclohexen-3-yloxy)-4-acetylamino-5-chlorobenzoate and 0.5 ml diethylaniline is placed under house vaccum and heated to 220° C. for 2 hours. This reaction mixture is then diluted with 40% ethylacetate/hexane and purified by dry column chromatography using the same solvent system as eluent. Three fractions are separated: 1. diethylaniline; 2. starting benzoate compound and 3. methyl 3-(3-hexenyl)-4-acetylamino-5-chlorosalicylate. The latter is used directly in the next step.

EXAMPLE 14

Methyl 1-acetylamino-2-chloro-5a,6,7,8,9,9a-hexahydrodibenzofuran-4-carboxylate

A mixture of 1.2 g of methyl 3-(3-hexenyl)-4-acetylamino-5-chlorosalicylate and 5 ml trifuloroacetic acid are stirred at room temperature overnight. The acid is removed under vacuum and the residue diluted with ether, washed with sodium bicarbonate, then water, dried and evaporated to dryness to give crude methyl 1-acetylamino-2-chloro-5a,6,7,8,9,9a-hexahydrodibenzofuran-4-carboxylate. This product is purified by flash chromatography using 10% ethylacetate/hexane to give pure product.

EXAMPLE 15

1-Amino-2-chloro-5a,6,7,8,9,9a-hexahydrodibenzofuran-4-carboxylic acid

To a solution of 0.3 g of sodium in 15 ml methanol is added 0.6 g of methyl 1-acetylamino-2-chloro-5a,6,7,8,9,9a-hexahydrodibenzofuran-4-carboxylate. Stirring is continued at 60° C. for two days. This is then diluted with 5 ml 1N sodium hydroxide and stirring continued at 60° C. overnight. The methanol is removed in vacuum, diluted with water, filtered, acidified with acetic acid, filtered, washed with water, dried over magnesium sulfate and evaporated to dryness to obtain 1-amino-2-chloro-5a,6,7,8,9,9a-hexahydrodibenzofuran-4-carboxylic acid. This is purified by crystallization from ethyl acetate/ether.

EXAMPLE 16

1-Amino-2-chloro-5a,6,7,8,9,9a-hexahydroibenzofuran-4-(N-1-azabicylco[2.2.2.]oct-3-yl]carboxamide To a cold solution of 0.3 g 1-amino-2-chloro-5a,6,7,8,9,9a-hexahydrodibenzofuran-4-carboxylic acid in 40 ml chloroform is added 0.3 g of triethylamine and then 0.2 g ethylchloroformate in 10 ml chloroform. Stirring is continued for 2 hours. This is then added to a cold mixture of 3 g 3-aminoguinuclidine dihydrochloride in 20 ml water containing 7.5 g $K_2CO_3$. Stirring is continued overnight. The reaction mxiture is then diluted with chloroform, the two layers separated and the chloroform layer washed twice with water, dried over magnesium sulfate and evaporated to dryness to give 1-amino-2-chloro-5a,6,7,8,9,9a-hexahydrodibenzofuran-4-(N-1-azabicylo[2.2.2.]oct-3-yl]carboxamide as an oily product.

Calculated: C 62.41; H 7.07; N 10.91; Found: C 62.84; H 7.00; N 10.63.

EXAMPLE 17

When 2-methoxy-4-amino-5-chlorobenzoic acid is replaced in Example 8 with 2-methoxy-4-aminobenzoic acid; 2-methoxy-4-methylamino-5-chlorobenzoic acid; 2-methoxy-5-sulfamylbenzoic acid; or 2-methoxy-5-methylsulfamyl benzoic acid then the products prepared following the procedures of Examples 8–16 are 1-amino-5a,6,7,8,9,9a-hexahydrodibenzofuran-4-(N-1-azabicylo[2.2.2.]oct-3-yl)carboxamide; 1-methylamino-2-chloro-5a,6,7,8,9,9a-hexahydrodibenzofuran-4-(N-1-azabicyclo[2.2.2.]oct-3-yl)carboxamide; 2-sulfamyl-5a,6,7,8,9,9a-hexahydrodibenzofuran-4-(N-1-azabicyclo[2.2.2.]oct-3-yl)carboxamide; or 2-methylsulfamyl-5a,6,7,8,9,9a-hexahydrodibenzofuran-4-(N-1-azabicyclo[2.2.2.]oct-3-yl)carboxamide.

EXAMPLE 18

When 3-aminoquinuclidine dihydrochloride in Examples 6, 7, 16 and 17 is replaced by the amines of Table I below, then the corresponding representative carboxamides of Table II below are prepared.

TABLE I 3-aminoquinuclidine which is 3-amino-1-azabicyclo[2.2.2.]octane

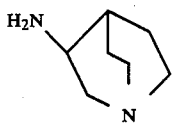

4-amino-1-azabicyclo[3.3.1.]nonane

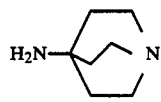

4-amino-1-azabicyclo[2.2.2.]octane

3-amino-9-methyl-9-azabicylco[3.3.1.]nonane

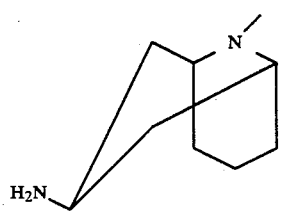

3-amino-7-oxo-9-methyl-9-azabicylo[3.3.1.]nonane

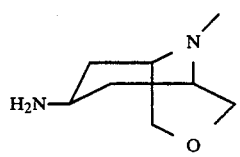

1-(p-fluorophenoxypropyl)-3-methoxy-4-aminopiperidine

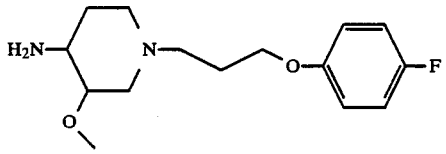

TABLE II 2-chloro-5a,6,7,8,9,9a-hexahydrodibenzofuran-4-(1-azabicyclo[3.3.1.]non-4-yl)carboxamide 2-chloro-5a,6,7,8,9,9a-hexahydrodibenzofuran-4-(1-azabicyclo[2.2.2.]oct-4-yl)carboxamide 2-chloro-5a,6,7,8,9,9a-hexahydrodibenzofuran-4-(9-methyl-9-azabicyclo[3.3.1.]non-3-yl)carboxamide 2-chloro-5a,6,7,8,9,9a-hexahydrodibenzofuran-4-(7-oxo-9-methyl-9-azabicylo[3.3.1.]non-3-yl)carboxamide 2-chloro-5a,6,7,8,9,9a-hexahydrodibenzofuran-4-(1-(p-fluorophenoxypropyl)-3-methoxy piperidin-4-yl)carboxamide 1-amino-2-chloro-5a,6,7,8,9,9a-hexahydrodibenzofuran-4-(1-azabicyclo[3.3.1.]non-4-yl)carboxamide 1-amino-2-chloro-5a,6,7,8,9,9a-hexahydrodibenzofuran-4-(1-azabicyclo[2.2.2.]oct-4-yl)carboxamide 1-amino-2-chloro-5a,6,7,8,9,9a-hexahydrodibenzofuran-4-(9-methyl-9-azabicyclo[3.3.1.]non-3-yl)carboxamide 1-amino-2-chloro-5a,6,7,8,9,9a-hexahydrodibenzofuran-4-(7-oxo-9-methyl-9-azabicylo[3.3.1.]non-3-yl)carboxamide 1-amino-2-chloro-5a,6,7,8,9,9a-hexahydrodibenzofuran-4-(1-(p-fluorophenoxypropyl)-3-methoxy piperidin-4-yl)carboxamide

EXAMPLE 19

When 3-bromocyclohexene of Examples 2 and 12 is replaced by
3-bromo-4-methylcyclohexene
3-bromo-5-methylcyclohexene
3-bromo-6-methylcyclohexene
then the corresponding products are prepared following Examples 2–18.

EXAMPLE 20

Methyl 1-acetylamino-2-chloro-6,7,8,9-tetrahydrodibenzofuran-4-carboxylate

A mixture of 1 g methyl 1-acetylamino-2-chloro-5a,6,7,8,9,9a-hexahydrodibenzofuran-4-carboxylate and 1 g of dichlorodicyanoquinone in 15 ml of benzene is stirred and heated at 80° C. in a sealed tube for 8 hours. The coooled reaction mixture is then diluted with benzene, filtered and evaporated to dryness. Purification by recrystallization from ethyl acetate/hexane gives pure methyl 1-acetylamino-2-chloro-6,7,8,9-tetrahydrodibenzofuran-4-carboxylate.

EXAMPLE 21

Methyl 1-acetylamino-2-chlorodibenzofuran-4-carboxylate

A mixture of 1 g methyl 1-acetylamino-2-chloro-6,7,8,9-tetrahydrodibenzofuran-4-carboxylate and 0.5 g of 5% palladium-charcoal is heated under nitrogen at 230° C. for 5 hours. The cooled residue is extracted with toluene and the solvent evaporated to dryness. The residue is crystallized from ethyl acetate/hexane to give methyl 1-acetylamino-2-chlorodibenzofuran-4-carboxylate.

EXAMPLE 22

1-Amino-2-chloro-6,7,8,9-tetrahydrodibenzofuran-4-carboxylic acid

1-Amino-2-chlorodibenzofuran-4-carboxylic acid

When the procedure of Example 15 is followed however methyl 1-acetylamino-2-chloro-5a,6,7,8,9,9a-hexahydrodibenzofuran-4-carboxylate is replaced by methyl 1-acetylamino-2-chloro-6,7,8,9-tetrahydrodibenzofuran-4-carboxylate or methyl 1-acetylamino-2-chlorodibenzofuran-4-carboxylate then the captioned products are prepared.

EXAMPLES 23

1-Amino-2-chloro-6,7,8,9-tetrahydrodibenzofuran-4-(N-1-azabicyclo[2.2.2.]oct-3-yl)carboxamide 1-Amino-2-chlorodibenzofuran-4-(N-1-azabicyclo[2.2.2.]oct-3-yl)carboxamide When the procedure of Example 16 is followed however, 1-amino-2-chloro-5a,6,7,8,9,9a-hexahydrodibenzofuran-4-carboxylic acid is replaced by 1-amino-2-chloro-6,7,8,9-tetrahydrodibenzofuran-4-carboxylic acid or 1-amino-2-chlorodibenzofuran-4-carboxylic acid then the captioned products are prepared.

EXAMPLE 24

Methyl 2-chloro-cis-5a,6,7,8,9,9a-hexahydrodibenzofuran-4-carboxylate

Methyl 2-chloro-trans-5a,6,7,8,9,9a-hexahydrodibenzofuran-4-carboxylate

A mixture of 9 g of methyl 3-(3-hexenyl)-5-chlorosalicylate and 20 ml trifluoroacetic acid is heated at 70° C. overnight. The cooled reaction mixture is diluted with hexanes, washed three times with water, dried and evaporated to dryness. The residue is purified with flash chromatography using 10% ethylacetate/hexane to give four fractions first fraction 2.2 g of material (mixture of at least two materials)
second fraction 2.2 g cis isomer
third fraction 1.6 g mixture of cis and trans isomers
fourth fraction 1 g trans isomer

EXAMPLE 25

2-Chloro-cis-5a,6,7,8,9,9a-hexadrodibenzofuran-4-carboxylic Acid

A mixture of 2 g methyl 2-chloro-cis-5a,6,7,8,9,9a-hexahydrodibenzofuran-4-carboxylate in 30 ml 1N sodium hydroxide and 5 ml dioxane is stirred at 60° C. for 5 hours. This is then diluted with water, filtered, acidified with acetic acid, extracted with ethyl acetate, dried over magnesium sulfate and evaporated to dryness to obtain an oily product which crystallizes on standing. This is recrystallyzed to obtain 2-chloro-cis-5a,6,7,8,9,9a-hexahydrodibenzofuran-4-carboxylic acid. (M.P. 132°–4° C.)

EXAMPLE 26

Following the procedure of Example 25 but using the trans isomer in place of this cis, the corresponding 2-chlor-trans-5a,6,7,8,9,9a-hexahydrodibenzofuran-4-carboxylic acid is prepared.

EXAMPLES 27

2-Chloro-cis-5a,6,7,8,9,9a-hexahydrodibenzofuran-4-(N-1-azabicyclo[2.2.2.]oct-3-yl)carboxamide 2-Chloro-trans-5a,6,7,8,9,9a-hexahydrodibenzofuran-4-(N-1-azabicyclo[2.2.2.]oct-3-yl)carboxamide Following the procedures of Examples 6 and 16 but substituting the cis and trans isomers of Examples 25 and 26, then the above captioned products are prepared.

EXAMPLE 28

1-Chloro-5a,6,7,8,9,9a-hexahydrodibenzofuran-4-(N-1-azabicyclo[2.2.2.]oct-3-yl)carboxamide Following the procedures of Examples 1–6 but substituting 4-chlorosalicylic acid in Example 1 for 5-chlorosalicylic acid, then the above captioned carboxamide is prepared.

We claim:

1. A compound of the formula

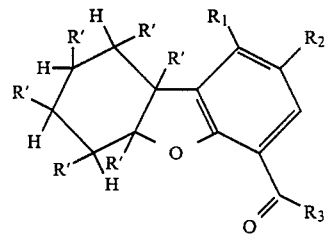

where $R_1$ is hydrogen, amino, alkylamino or halo; $R_2$ is hydrogen, halo, sulfamyl; alkylsulfamyl or alkylsulfonyl; R' is hydrogen or alkyl; and $R_3$ is hydroxy, halo, alkoxy or aralkoxy; provided that R', $R_1$ and $R_2$ are not all hydrogen at the same time.

2. A compound according to claim 1 which is:

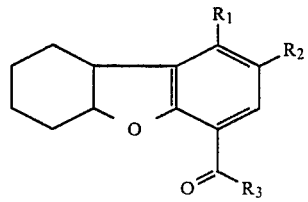

3. A compound according to claim 2 where $R_2$ is halo.
4. A compound according to claim 2 where $R_1$ is amino.
5. A compound according to claim 2 where $R_1$ is amino and $R_2$ is halo.
6. A compound according to claim 3 where halo is chloro or bromo and $R_3$ is hydroxy.
7. A compound according to claim 4 where $R_3$ is hydroxy.
8. A compound according to claim 2 where $R_2$ is chloro or bromo and $R_3$ is hydroxy.
9. A compound according to claim 1 which is in the 5a,9a cis configuration.
10. A compound according to claim 3 which is in the 5a,9a cis configuration.
11. A compound according to claim 10 which is 2-chloro-cis-5a,6,7,8,9,9-hexahydrodibenzofuran-4-carboxylic acid.

* * * * *